(12) United States Patent
Teichman et al.

(10) Patent No.: US 7,749,553 B2
(45) Date of Patent: Jul. 6, 2010

(54) METHOD AND SYSTEM FOR COATING A MEDICAL DEVICE USING OPTICAL DROP VOLUME VERIFICATION

(75) Inventors: Eyal Teichman, Hod-Hasharon (IL); Avner Schrift, Rishon-Le-Zion (IL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1507 days.

(21) Appl. No.: 11/047,282

(22) Filed: Jan. 31, 2005

(65) Prior Publication Data
US 2006/0172060 A1 Aug. 3, 2006

(51) Int. Cl.
*B05C 11/00* (2006.01)
*C23C 16/52* (2006.01)
*B41J 29/373* (2006.01)

(52) U.S. Cl. ............... 427/2.1; 427/8; 427/9; 427/10; 118/712; 118/713; 118/665; 118/688; 118/694; 347/19; 222/630

(58) Field of Classification Search ........... 427/8–10; 118/665, 688, 694
See application file for complete search history.

(56) References Cited

U.S. PATENT DOCUMENTS

| | | | | |
|---|---|---|---|---|
| 4,322,449 A * | 3/1982 | Voss et al. | ................. | 427/2.14 |
| 5,666,325 A * | 9/1997 | Belser et al. | ................. | 367/95 |
| 6,173,864 B1 * | 1/2001 | Reighard et al. | ............... | 222/55 |
| 6,213,354 B1 * | 4/2001 | Kay | ............................ | 222/420 |
| 6,220,075 B1 * | 4/2001 | Papen et al. | .................. | 73/1.74 |
| 7,121,642 B2 * | 10/2006 | Stoessel et al. | ............... | 347/19 |
| 2001/0050294 A1 * | 12/2001 | Plattner et al. | .............. | 222/630 |
| 2002/0079325 A1 * | 6/2002 | Estelle | ......................... | 222/1 |
| 2003/0125800 A1 * | 7/2003 | Shulze et al. | .............. | 623/1.15 |
| 2004/0231594 A1 * | 11/2004 | Edwards et al. | ............. | 118/719 |
| 2005/0083538 A1 * | 4/2005 | Arnold et al. | ............... | 356/627 |

FOREIGN PATENT DOCUMENTS

GB          2365523 A          2/2002

OTHER PUBLICATIONS

PCT International Search Report, PCT/IB2006/000245, Jun. 7, 2006.

* cited by examiner

*Primary Examiner*—Timothy H Meeks
*Assistant Examiner*—Cachet I Sellman
(74) *Attorney, Agent, or Firm*—Vidas, Arrett & Steinkraus P.A.

(57) ABSTRACT

A method and apparatus for controlling coating material deposition on to a medical device. Images of material drops in flight are captured and an average single drop volume value is calculated by conversion of the captured drop images to a volume measurement. The average single drop volume value is used to calculate a total number of drops necessary to apply a desired amount of coating. Alternately, material is applied and the amount of material deposited is accumulated and adjustments are made to deposit only a desired amount of coating material. A drop volume is determined for either every drop or a sampling of drops as the drops are being applied. Adjustments to the coating process include changing drop size and changing a number of drops to be deposited.

7 Claims, 13 Drawing Sheets

METHOD AND SYSTEM FOR COATING A MEDICAL DEVICE USING OPTICAL DROP VOLUME VERIFICATION

FIELD OF THE INVENTION

The present invention relates to a method and apparatus for depositing a coating material, such as a drug or therapeutic agent, onto a medical device and, more particularly, the present invention relates to a method and apparatus for verifying material drop size and volume of any material being deposited.

BACKGROUND OF THE INVENTION

Today, many medical conditions are treated by placing medical devices or appliances within a patient. Many medical conditions necessitate the use of these medical devices for supporting of blood vessels or other lumens within the body that have been re-enlarged following, for example, cardio balloon angioplasty.

With regard to angioplasty, typically an endovascular implant known as a stent is placed within the blood vessel. A stent is usually tubular in shape and may have a lattice or connected-wire tubular construction. The stent is usually placed within the vessel in a compressed state and then allowed to expand. Self-expanding and balloon-expandable stents are well known. The support provided by a stent prevents the vessel from either closing, referred to as restonosis, or suffering spasms shortly after the angioplasty procedure.

In addition to the structural support provided by a stent, it is known to provide coatings containing medicines upon an outer surface of the stent. Here, the outer surface is meant to indicate that surface that is in direct contact with the vessel wall. The coating on the outer surface of the stent is absorbed by the vessel wall, and the medicine in the coating is absorbed.

There are many proposed methods and systems for providing this medicinal coating to the stent. The methods are known to include dipping, contact coating, spraying and electrostatic deposition.

The precise control of the coating process is important for a number of reasons including, but not limited to, the cost of the medicine in the coating, the mechanics of the stent itself in that the coating should not interfere with proper operation of the stent and the requirements, at least in the United States, of an FDA regulated device.

SUMMARY OF THE INVENTION

While there are many different methods known for placing a coating on a stent, it is important to be able to accurately control the amount of coating that is placed thereon. The amount of coating placed on the stent is directly proportional to the amount of beneficial medicine that is provided to the patient. The present invention provides for a mechanism to ensure that the correct amount of coating and, therefore, medicine, is placed on the medical device. This control allows for more accurate dispensing of medication, better inventory control in the manufacturing process and better performance where it is needed most, i.e., in the patient's body.

The present invention provides a method and apparatus for combining an "in-flight" volume measurement of drops of coating material as these drops are deposited on a stent surface by a drop on demand (DOD) or an ink type applicator. An image of one or more drops of coating material as the drops are being applied to the stent is captured and converted into digital information from which a drop volume can be determined. Either every drop can be measured or a statistically relevant sampling of drops can be performed.

The system measures each drop's volume and compares it to an expected or desired single drop volume. From this measured drop volume, an accumulated volume can be maintained. While the drop on demand applicator may be set or configured to expel drops of a particular volume, a malfunction, e.g., clogging, volume change, or any other type of mis-performance of the applicator will be detected or measured by the present invention. The present invention will keep track of a total volume of material that has been applied and compare this measured volume to the expected volume.

If, at the end of the application process, which can consist of a million discrete drops deposited on the stent's surface, it is determined that the actual volume deposited is, for example, less than the desired amount, then the system can determine an additional number of drops that are necessary in order to attain the desired total volume. Alternatively, if the total volume is obtained prior to the placement of the entire number of drops set for deposition, the system may halt further deposition of coating material.

Further, this system can adjust the size of the drops that are being deposited in order to either compensate for not enough material being deposited or too much material being deposited. If the system detects that the drop size is out of an acceptable range, then either an operator is notified or the process stopped entirely.

In one embodiment of the present invention, a method of controlling an amount of material deposited on a medical device comprises determining an applied single drop volume value; calculating a total number of drops of material necessary to deposit a desired total volume of material as a function of the applied single-drop volume value; and depositing the calculated total number of drops of material on the medical device.

Further, determining the applied single drop volume value comprises: configuring a coating applicator with a predetermined first set of parameters; causing the coating applicator to fire a plurality of drops of material; capturing an image of at least two drops of the plurality of drops in-flight as fired by the coating applicator; calculating an average drop volume value of the at least two in-flight drops as a function of the captured image; and setting the applied single drop volume value to be the calculated average drop volume value.

In one embodiment determining the applied single drop volume and calculating the total number of drops necessary are performed prior to depositing the calculated number of drops on the medical device.

BRIEF DESCRIPTION OF THE DRAWINGS

The above and further advantages of the invention may be better understood by referring to the following description in conjunction with the accompanying drawings in which.

DETAILED DESCRIPTION

Figure 1:
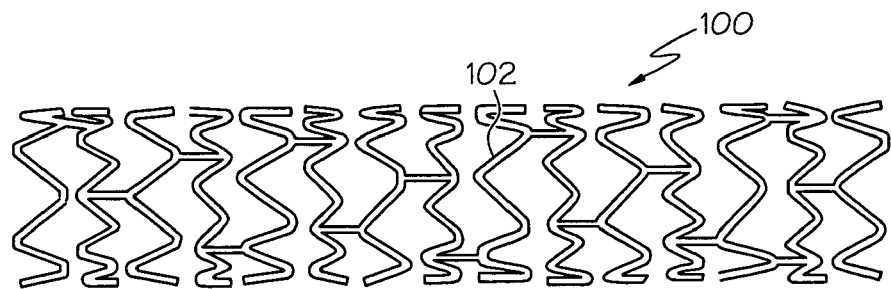
FIG. 1 is a schematic diagram of a known stent.

A stent 100 is a medical device or implant and, as shown in FIG. 1, is generally tubular in shape and typically has a lattice or tubular construction that is expandable. The lattice construction includes a strut 102 and has also been characterized as having a plurality of longitudinally connected ring portions. Throughout the following description, reference to a strut 102 is meant to include the portions of the stent 100 that either make up the ring or the portions of the lattice structure that interconnect one ring with another.

Figure 2:
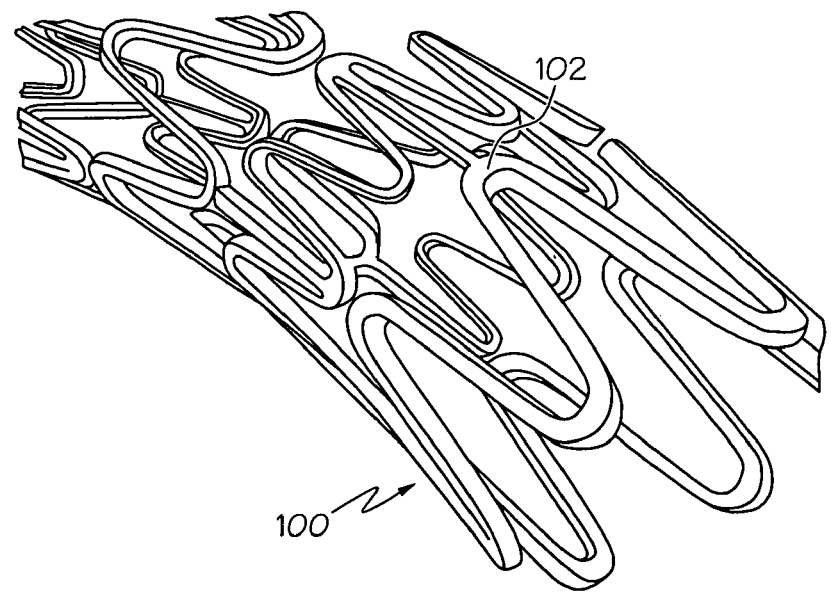
FIG. 2 is a close-up schematic diagram of the stent of FIG. 1.

Each strut has an exterior surface, an interior surface and lateral or side surfaces connecting the exterior and interior surfaces. In this description, reference to an exterior surface of a stent or strut is meant to describe the surface that is in contact with the vessel wall. The interior surface would be that surface that is in contact with the luminal flow, e.g., blood flow in a blood vessel, when the stent is in place. As shown in FIG. 2, a strut may have a cross section that is substantially rectangular. Alternatively, some stents are known to be made with struts that have an oval, elliptical or circular cross section. The present invention is not dependent on a particular stent's geometry or topology including the strut cross section, number of ring sections, orientation of interconnecting struts, etc.

One known system and method for coating a stent involves the application of the coating material by a drop-on-demand (DOD) applicator. In drop-on-demand, a predetermined number of drops of a particular size are either actively or passively released and directed toward a surface of the stent. This mode of application is also referred to as jetting when a sequence of drops is released. An example of such technology is available from InkJet Technology, Inc. of San Jose, Calif. The use of a drop-on-demand technology to apply a coating material to a stent is described in U.S. publication No. 2003/0207019, published Nov. 6, 2003, titled STENT COATING DEVICE by Shekalim et al. which is assigned to the same assignee as the current application and which is herein incorporated by reference in its entirety.

Figure 3:
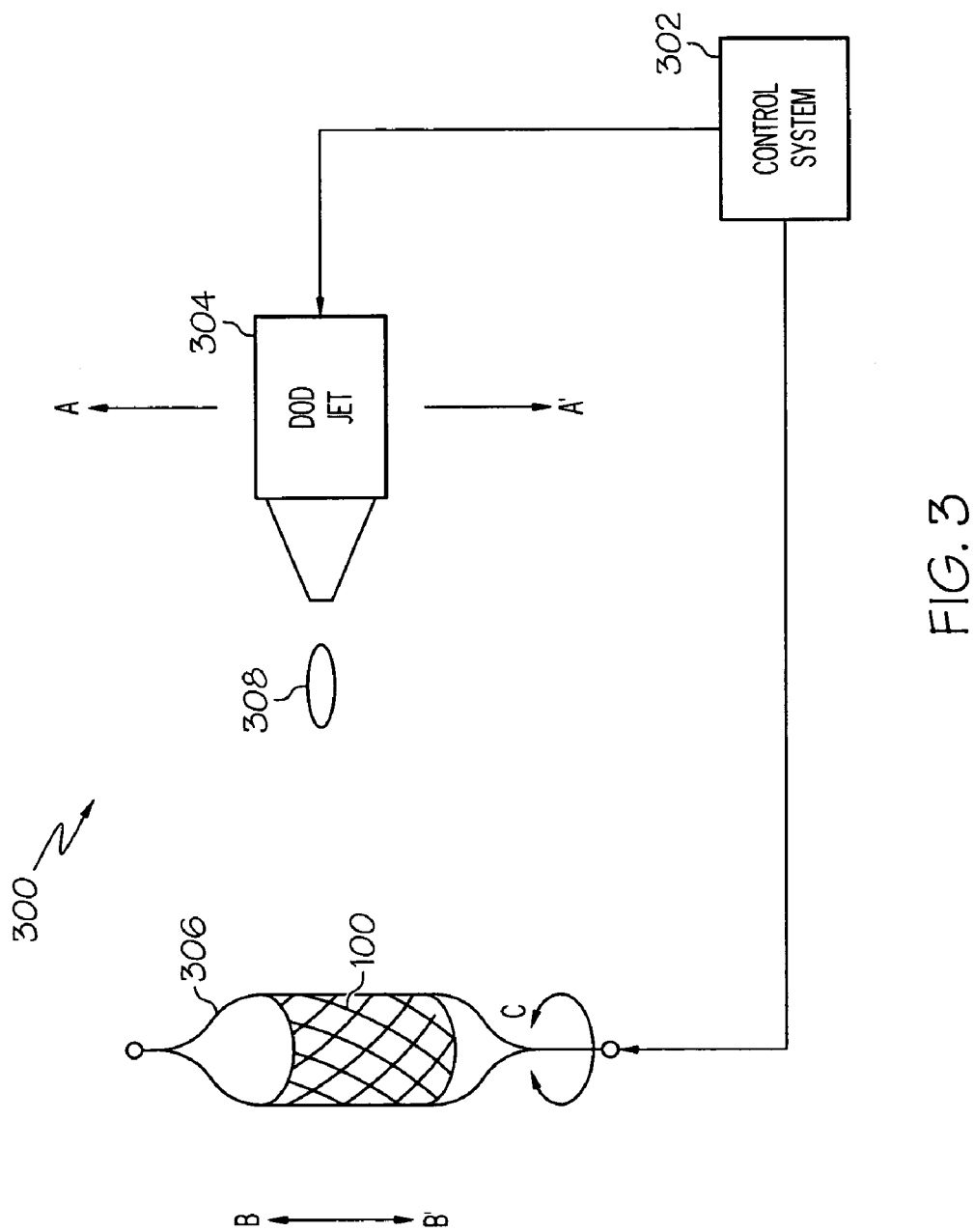
FIG. 3 is a schematic diagram of a stent coating apparatus.

In general, a drop-on-demand coating system 300 includes a control system 302 coupled to a drop-on-demand (DOD) applicator 304 and to a mandrel 306 on which a stent 100 is positioned, all as represented in the schematic block diagram shown in FIG. 3. In operation, the control system 302 directs the DOD applicator 304 to eject a drop of coating material toward the stent 100. The control system 302 positions the DOD applicator 304 with respect to those portions of the stent 100 on which it is desired to place the coating material. The control system 302 is operable to move the DOD applicator 304 relative to the surface of the stent 100 by either rotating the mandrel 306 on which the stent 100 is located, as shown by arrow C, moving the DOD applicator 304 linearly as shown by arrow A-A', moving the mandrel/stent along a linear direction represented by arrow B-B' or some combination of the foregoing movements.

The control system 302 positions the DOD applicator 304 with respect to the stent 100 in order to deposit the drops 308 in only the desired areas. This positioning can include moving the applicator 304 relative to the stent 100 by either preset mechanical positions, visually scanning the stent 100 to identify the locations on which the coating is to be deposited or "following along" the lattice pattern of the stent. For purposes of the present invention, however, the mechanism used to position the DOD applicator 304 over the stent 100 is not a limitation of the present invention unless specifically recited in the claims.

The DOD applicator 304 responds to control signals from the control system 302 with respect to when to eject a drop 308 toward the surface of the stent 100. The control system 302 provides a signal to select a desired size of the drop 308 and its acceleration toward the stent 100. One of ordinary skill in the art would understand the types of signals necessary to cause the DOD applicator 304 to emit a drop 308 with the desired characteristics.

The DOD applicator 304 is, for example, a piezoelectric device with a nozzle through which a drop 308 is ejected. In operation, however, because of characteristics of the coating material including, but not limited to, viscosity, temperature, density and the like, DOD applicator 304 performance may become impaired. One mode of impairment is a clogged aperture. This may lead to a situation where, although the control system 302 is sending signals to the DOD applicator 304 to eject a drop 308, due to clogging, however, the actual drop that is emitted is either not the correct volume or may be totally missing. The present invention provides a mechanism by which proper drop volume can be confirmed and, in addition, total deposited volume is measured.

According to an embodiment of the present invention, an image of a drop 308 in flight from the DOD applicator 304 to the stent 100 is captured. This captured image is then processed and a drop volume is calculated. With the present invention, the DOD applicator 304 can be monitored to assure that the appropriate amount of coating material, either on a per drop basis or on a cumulative basis, is being deposited.

Figure 4:
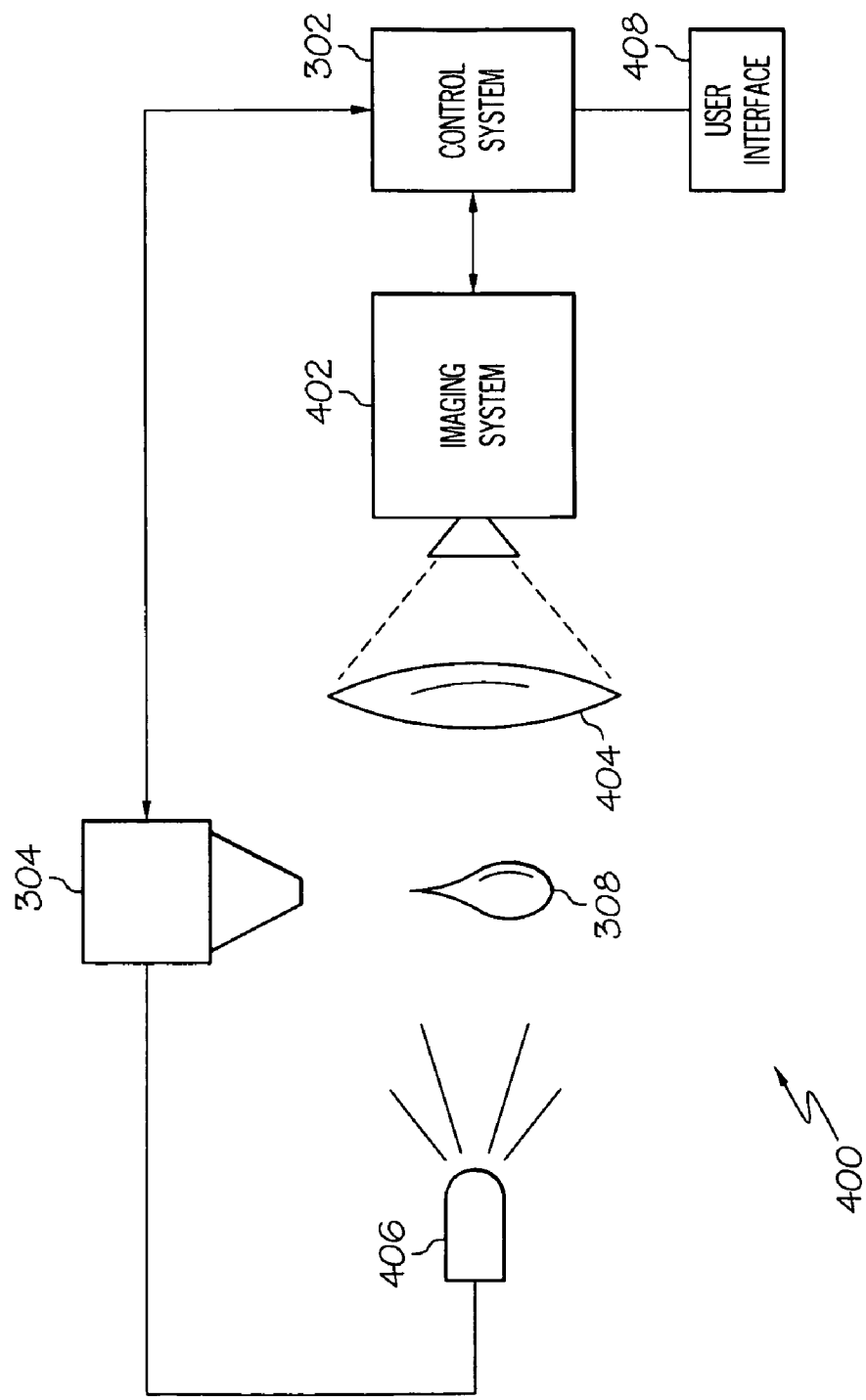
FIG. 4 is a schematic diagram of a drop volume measuring system.

Referring to FIG. 4, a drop volume system 400 includes the control system 302 coupled to the DOD applicator 304 and an imaging system 402. The imaging system 402 operates in conjunction with a lens 404, although the lens 404 can be incorporated into the imaging system 402 directly. A strobe light 406 is coupled to the DOD applicator 304. A user interface 408 is coupled to the control system 302. The user interface 408 allows a user to input the user selectable attributes of the system, e.g., material type, drop size, drop velocity, total volume to deposit, temperature, etc, to monitor operation of the system and receive alerts indicating how the process is functioning. The user interface 408 may present this information via a display device such as a computer monitor and may use a graphical user interface as is known in the art. The drop volume system 400, in one embodiment of the present invention, is sized to fit on a desktop.

In operation, when a drop 308 is ejected from the DOD applicator 304 the strobe light 406, synchronized to the DOD applicator 304, flashes to illuminate or "freeze" the drop 308 and an image of the drop 308 is acquired through the lens 404 into the imaging system 402. Within the imaging system 402, the image of the drop 308 is stored within either memory or on a storage device such as a disk drive.

One of ordinary skill in the art will understand the operation of an imaging system 402 for capturing an image. An example of an imaging system 402 is the Visisizer product available from Oxford Lasers of Littleton, Mass. An imaging system such as this one would include a charge coupled device (CCD) with a resolution of, for example, 1,018×1,018 at eight bits. The selection and characteristics of the imaging system 402 are not limitations of the present invention unless specifically recited in the claims appended hereto.

The captured image of the drop 308 is processed either in the imaging system 402 or the control system 302 to convert the image to a drop volume measurement. The image is digitized and, based on a number of pixels in the digitized image, a drop volume can be determined.

While the image captured is a two-dimensional representation of a three-dimensional object, based on the characteristics of drops, the two-dimensional representation can be extrapolated to determine its volume. When the system is calibrated, through a procedure to be described below, each pixel represents a specific size from which the volume can then be calculated. In general, an accurate measurement of the drop volume can be obtained as the drop 308 tends to have a consistently circular cross-section in the plane parallel to the direction from which the image is taken, i.e., substantially perpendicular to a direction in which the drop is moving.

Figure 5:
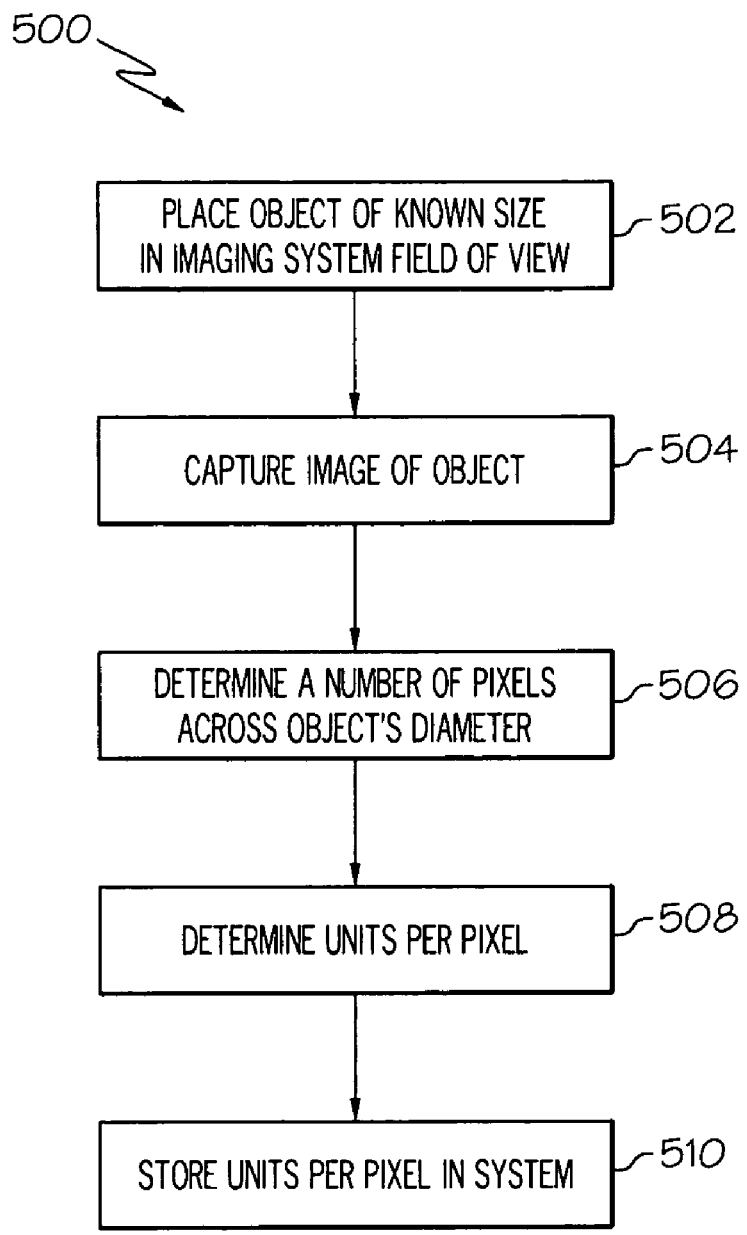
FIG. 5 is a flowchart for a calibration procedure.

A calibration procedure is implemented in order to determine a unit of measurement for each pixel in a captured image. With respect to the calibration procedure 500 shown in FIG. 5, initially an object of known size is placed in the imaging system field of view at step 502. In one embodiment, the object of known size is a black circular dot. This dot is placed at the same point at which the drop 308 is imaged in the system. In this manner, variables such as distance from a drop to camera lens, lighting and other characteristics are accounted for. At step 504, an image of the dot is captured. Subsequently, a number of pixels across the diameter of the object is determined at step 506. As the diameter of the object is known, the units of measurement per pixel can then be calculated at step 508. This value is then stored as the unit per pixel value at step 510.

The calibration procedure 500 may be run either at the beginning of a batch run of stents to be coated, prior to each stent or manually initiated by an operator of the system. Any image of a known size may be used as the calibration image as long as the edges of the images can be identified. One of ordinary skill in the art would understand how the edges of an image could be identified. The actual size of the calibration image can be entered by an operator to facilitate the calibration calculation.

Figure 6A:
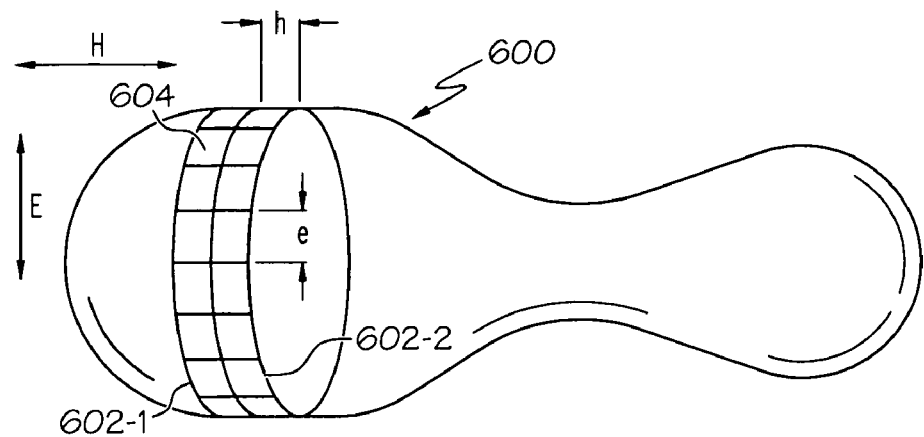
FIGS. 6A-C are schematic representations of a drop volume determination process.
Figure 6B:
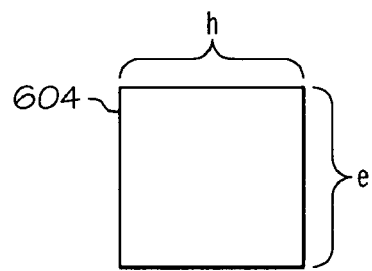

In one embodiment of the present invention, the volume of a single drop 308 is calculated by applying a "slicing" analysis of the drop 308 image. As shown in FIG. 6A, which is meant to be an aid in understanding the description and not a representation of an actual slicing of a drop, a drop image 600 is divided into a number of slices 602, with two slices 602-1, 602-2 represented. As schematically shown, each slice 602 can be represented as having a circular cross-section. Thus, each slice 602 would be represented as a cylinder with a height in the direction shown by an arrow H having a value h, corresponding to the calibrated pixel. The diameter of the cylinder or slice 602 would be the number of pixels 604 in the direction shown by an arrow E multiplied by a length e of the calibrated pixel 604. As shown in FIG. 6B, a pixel 604 would have a characteristic height h in the H direction and a length e in the direction E.

Figure 6C:
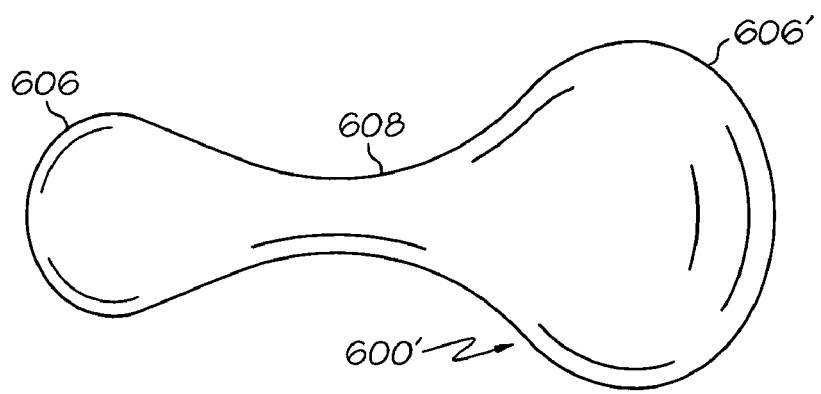

As shown in FIG. 6C, a drop image 600', in some instances, may be characterized as consisting of a smaller ball shape portion 606, coupled to a larger ball shape portion 606' by a cylinder portion 608. These portions of the drop image 600, 600' are identified by the present invention and a volume corresponding to each portion is then calculated where the total of these volumes represent the volume of the drop.

As an example only for the purposes of further clarifying an embodiment of the present invention, as shown in FIG. 6A, the slice 602-2 would have a height of h and a diameter of 8*e. The area of this slice would then be $h*\pi*(4e)^2$. The drop image 600 is divided into the slices and the volume for each slice is determined and accumulated to arrive at a calculated drop volume.

In an alternate calibration procedure, according to another embodiment of the present invention, the DOD applicator 304 is configured to expel a drop of a desired volume. The DOD applicator 304 is caused to eject one or more drops toward a target. In this instance, however, the target is an item that is easily removable from the system. Images of the drops are captured in-flight and a volume calculation, as described above, is performed. This calculated volume is compared to the actual volume by removing the item on which the drops were deposited and determining the actual volume that was deposited. This actual volume can be determined by measuring a difference in weight between the device without the coating drops and the device after the coating drops have been applied. As the density of the coating material is known, as well as the number of drops deposited, adjustments to the optical drop volume measurement system can be programmed as part of this calibration procedure.

One of ordinary skill in the art would understand that there are any number of other methods for identifying a drop from a captured image and subsequently determining that drop's volume. An example of such a system is drop sizing software available from Oxford Lasers known as VisiSize.

Figure 7:
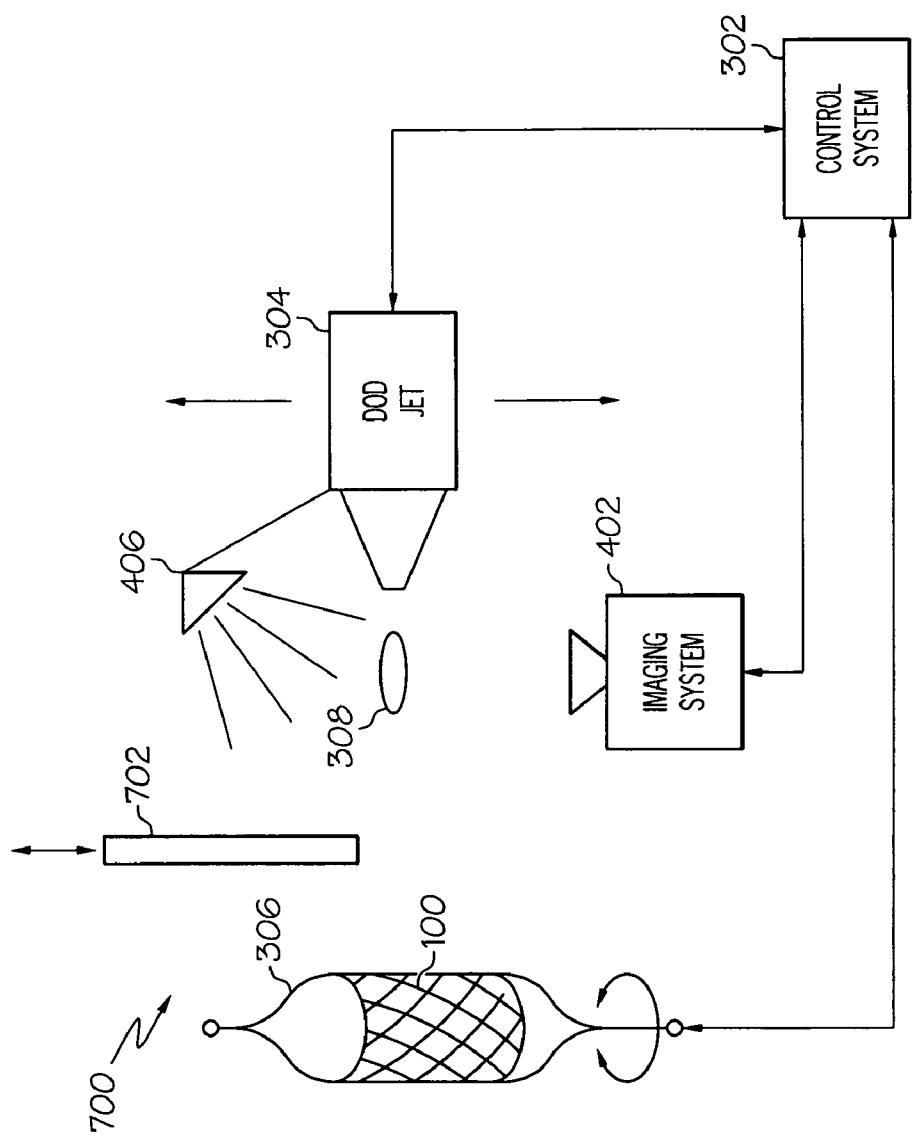
FIG. 7 is a schematic diagram of one embodiment of the present invention.

As schematically shown in FIG. 7, an on-line system 700 according to one embodiment of the present invention is displayed. The control system 302 controls the operation of the DOD applicator 304 and the mandrel 306 on which the stent 100 is positioned. The imaging system 402 is also coupled to the control system 302 and the images that the imaging system 402 captures of the drop 308 in flight are processed in either the imaging system 402 or the control system 302 or a combination thereof. In the on-line system 700, the imaging system 402 is located to capture images of the drops 308 as the drops 308 are fired toward the stent 100. As will be described further below, the control system 302 responds accordingly to the measured drop volume.

In one mode of operation of the on-line system 700, a blocker 702 is positionable between the stent 100 and the DOD applicator 304. When the blocker 702 is in place, it will prevent any drop 308 of material from landing on the stent 100. The blocker 702 may be moved in and out of position either under control of the control system 302, manually by an operator or by some other mechanism which would easily be understood by one of ordinary skill in art.

In one embodiment of the present invention, the blocker 702 is positioned between the stent 100 and the DOD applicator 304 in order that one or more drops 308 may be expelled from the DOD applicator 304 and the system can confirm that the drop volume is correct. This would be advantageous when, for example, in the midst of a coating application the system determines that the drop size is incorrect. The blocker 702 can be put into place and the size of the drop adjusted under control of the control system 302. A number of test drops could then be fired to confirm that the changes have resulted in the desired effect. While this may result in a loss of a small amount of coating material, this embodiment of the present invention allows for stopping and restarting a coating application procedure without having to discard the material already placed on the stent that is being coated.

The blocker 702 may be made of a material sufficient to absorb the coating material. Once the blocker 702 is saturated, it could be replaced with fresh material. Alternatively, the blocker 702 may be either include a suction or vacuum system to pull in or capture the coating material or a reservoir or spittoon.

Figure 8:
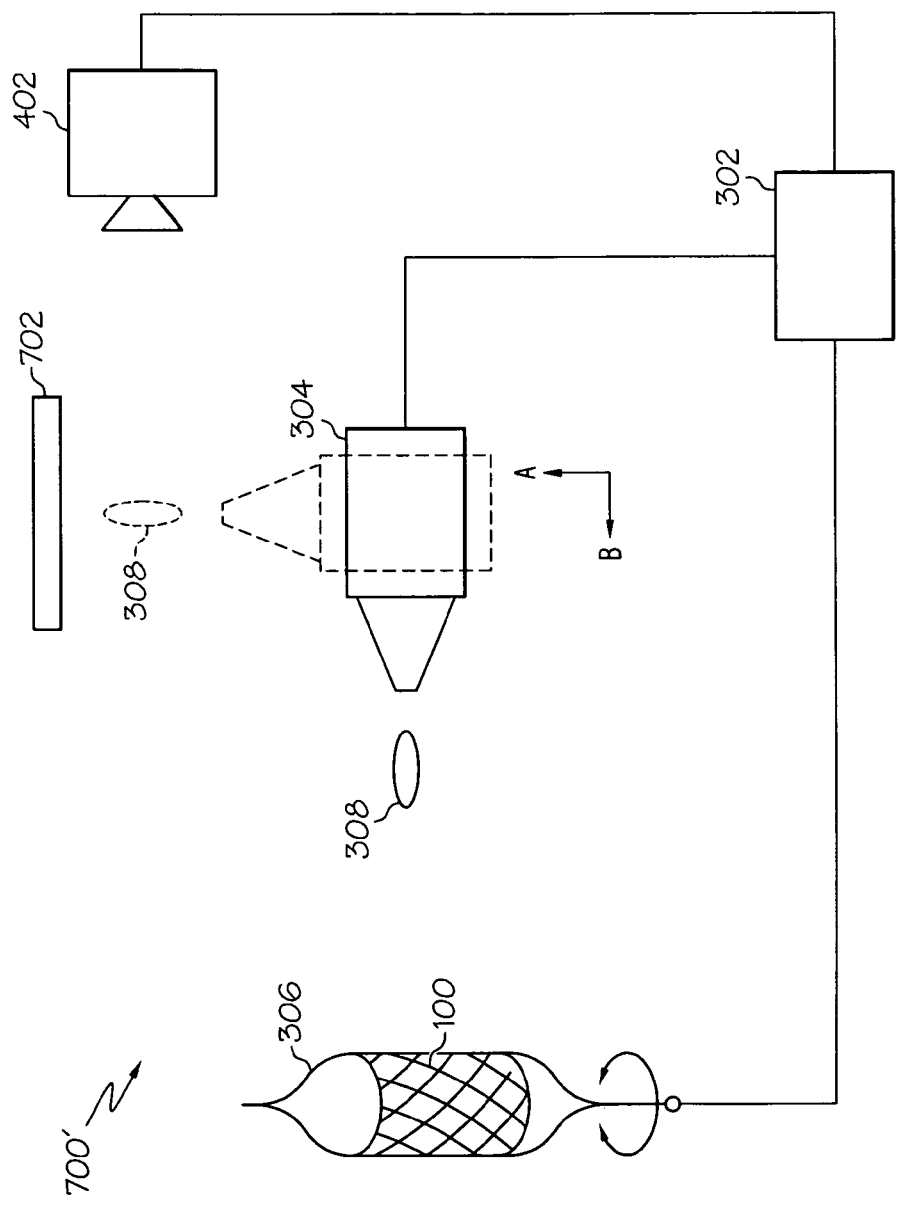
FIG. 8 is a schematic diagram of another embodiment of the present invention.

In an alternate embodiment of the present invention, as shown in FIG. 8, the images of the drops 308 are not captured as the drops 308 are directed toward the stent 100. In an "off-line" system 700', the DOD applicator 304 is turned away from the stent 100, as shown by the dotted lines. The imaging system 402 is positioned to capture images of the drops 308 as the drops are fired. An average drop volume value is calculated. To coat the stent 100, the DOD applicator 304 is turned toward the stent 100. It should be noted, of course, that the representation of the on-line and off-line systems, in each of these figures, is merely to aid in the description and does not convey any scale or other limitations of the invention except those that are recited in the appended claims.

The DOD applicator 304 is mounted in order to be rotated either by manual operation or under control of the control system 302. In one non-limiting example, the DOD applicator 304 is mounted on a stepper motor controlled by the control system 302. One of ordinary skill in the art understands that there are other equivalent mechanisms for providing a rotatable applicator.

While the foregoing system has been described with a stent 100 positioned on a mandrel 306 to receive the coating material, another embodiment of the present invention is directed to the system where the stent 100 is mounted on a balloon catheter. Thus, in the foregoing description where a mandrel 306 was described as being positioned, i.e., rotated or linearly moved, by the control system 302, another embodiment of the present invention includes a stent mounted on a balloon catheter on which the stent is delivered and placed within a patient. Of course, one of ordinary skill in the art will readily see that there are many equivalent mechanisms for mounting a stent or medical device to receive a coating material.

Figure 9:
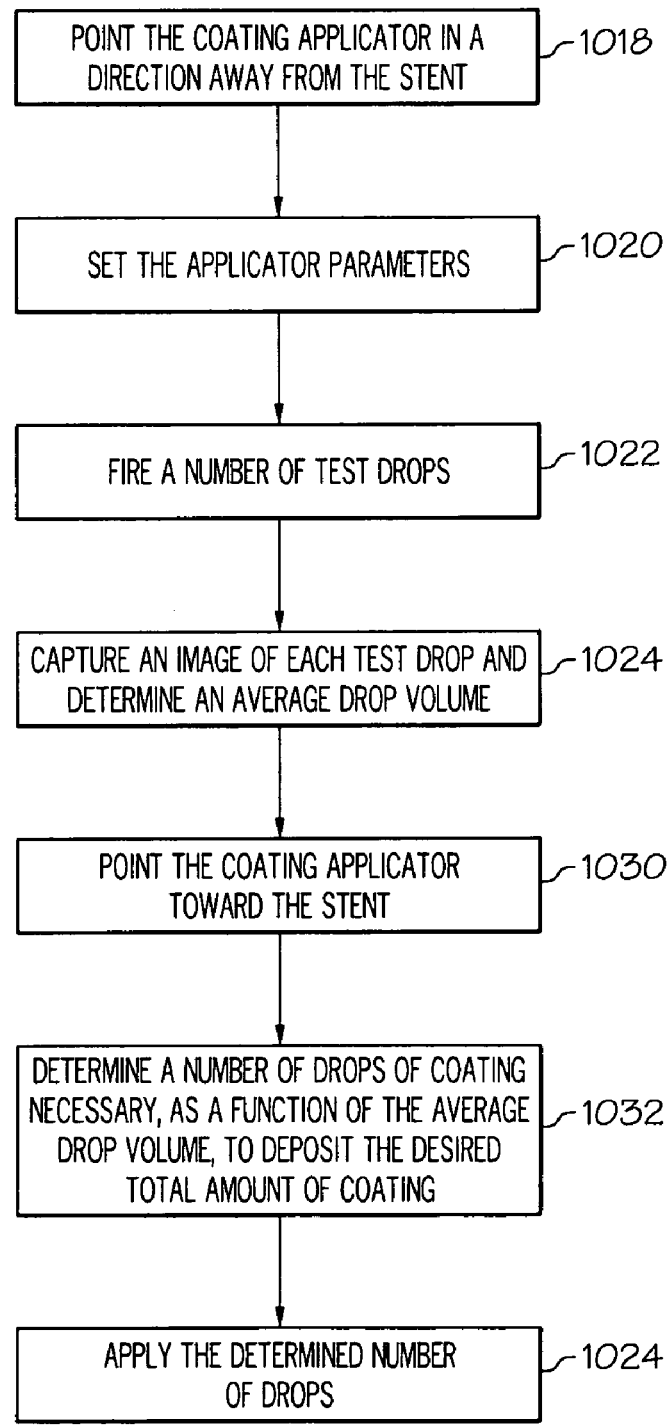
FIG. 9 is a flowchart of a process according to an off-line embodiment of the present invention.

Operation of the off-line system 700' will now be described with reference to the flowchart in FIG. 9. Initially, the DOD applicator 304 is turned in a direction away from the stent, step 1018, and the applicator 304 is configured, i.e., its parameters for velocity, size, frequency, etc., are set, step 1020. A number of test drops 308 are then fired, step 1022. The number of drops is chosen to present a statistically significant number over which an average volume can be determined by sampling and to allow for settling of the DOD applicator 304.

In one embodiment, 1000 drops are sampled, although this number is for example only and not intended to limit the present invention. The test drops 308 are captured in either a spittoon or a material similar to that of the blocker 702. The imaging system 402 captures images of the test drops 308 in flight and an average drop volume for this setting of the applicator 304 is then calculated, step 1024. The applicator is then re-oriented toward the stent 100, step 1030. The calculated average drop volume value is then used to determine a number of drops necessary to deposit a desired amount of coating, step 1032. The determined number of drops are then applied to the stent, step 1034, with the applicator set to the same parameters as were used for determining the average drop volume.

In another embodiment of the "off-line" mode of operation, the average single drop volume may be determined for different combinations of coating applicator parameters. Thus, the coating applicator's settings can be changed and the corresponding single drop average volume is used to determine the number of drops that need to be deposited. The coating applicator's parameters can be changed "on-the-fly" and a new number of needed drops can be calculated. As a non-limiting example, the coating applicator may be configured, according to a first set of parameters, to deposit a first plurality of a first number of drops of a first size to provide a first volume of material and then configured, according to a second set of parameters, to deposit a second plurality of a second number of drops of a second size. The second plurality of drops may be of the same or different material as the first plurality of drops. The respective average single drop volume for each of the first and second sets of parameters will have already been determined and stored for later access. When the off-line measurements are repeated, the single drop volume value can be updated.

In yet another mode of operation of the off-line system 700' embodiment, the average drop volume can be regularly re-checked during operation of the coating system. The frequency of this check can be based on, for example, a total number of drops of material deposited over some predetermined time period, a number of different stents that have been coated over a period of time, total volume of material deposited, number of hours of operation since last check or a combination of any of the foregoing. One of ordinary skill in the art will understand that there may be other criteria for determining when it might be beneficial to check the drop volume and the foregoing list is not intended to limit the present invention.

Figure 10:
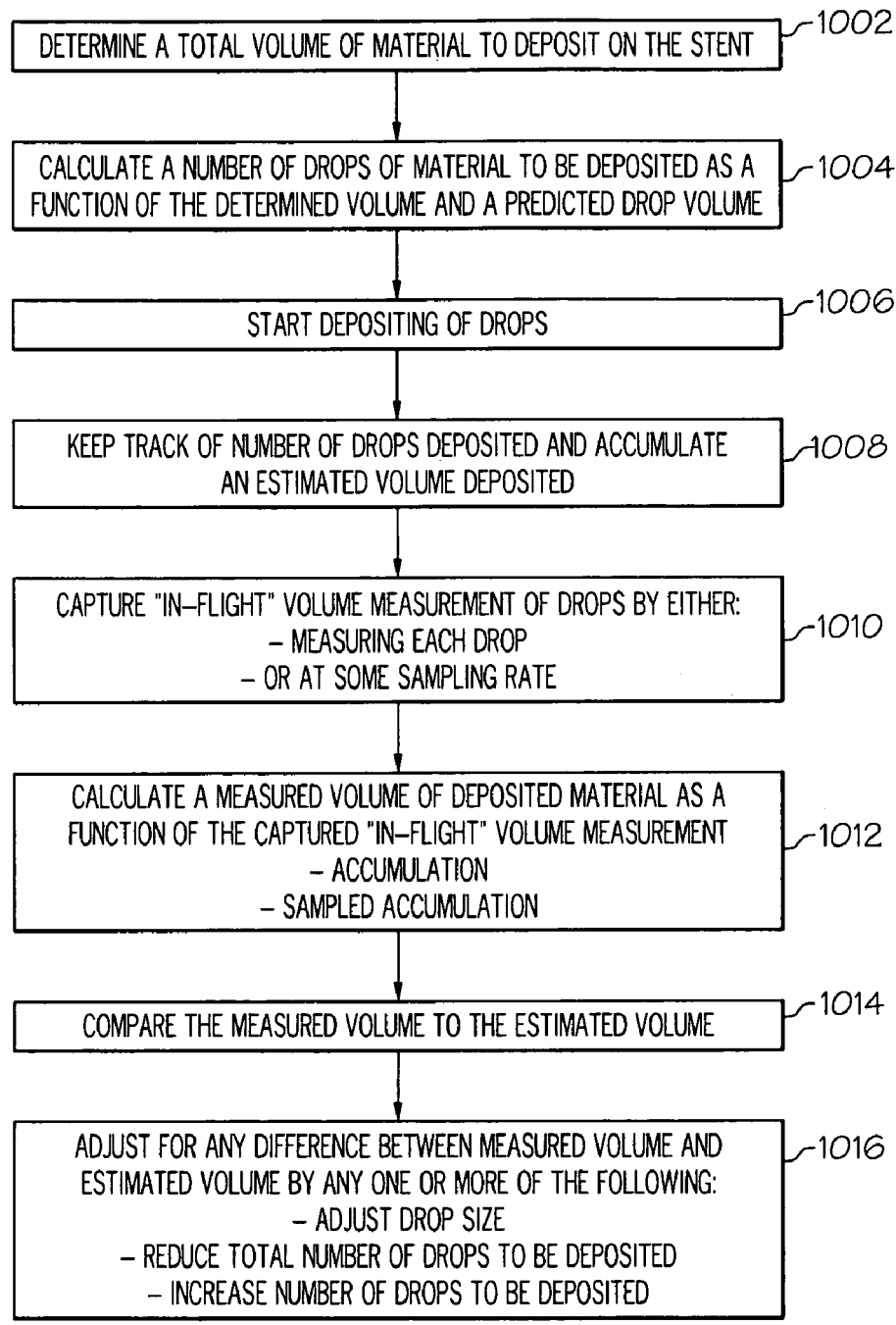
FIG. 10 is a flowchart for processes according to an on-line embodiment of the present invention.
Figure 11:
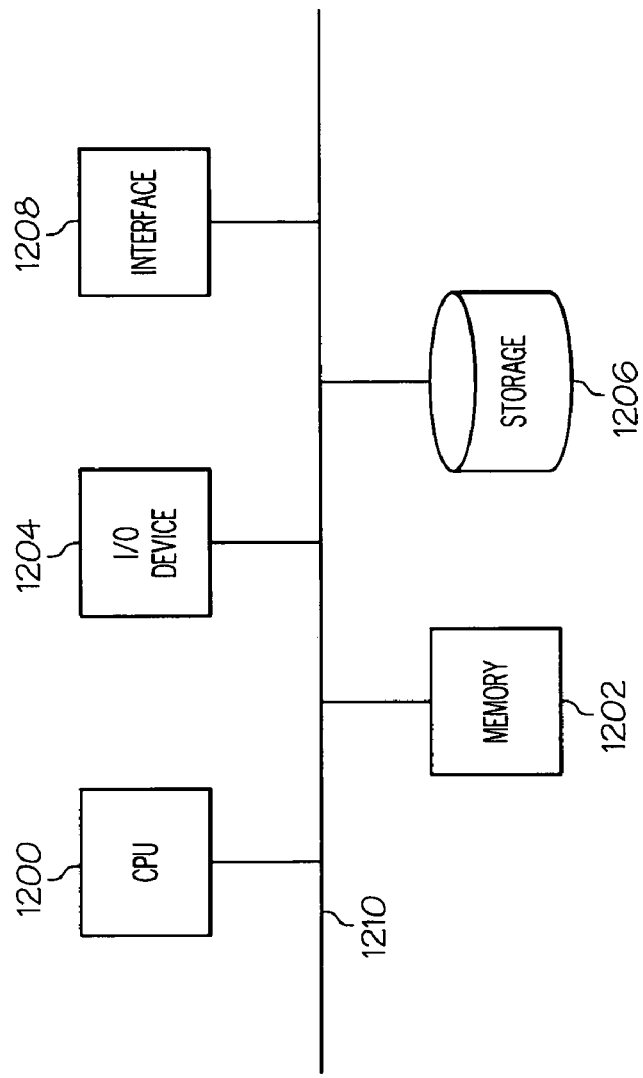
FIG. 11 is a block diagram of a computing device.

In operation of the on-line system 700, as per the flowchart of FIG. 10, starting in step 1002, a total volume of material to be deposited on a medical device is determined. A number of drops of material to be deposited is calculated as a function of the determined volume and a predicted or predetermined single drop volume, step 1004. The predicted single drop volume is a value that may be chosen based on an expected drop volume as the DOD applicator 304 is set in accordance with, for example, the manufacturer's specification or operating instructions. The predicted single drop volume may also be chosen by the operator based on past experience with the applicator. The drops are deposited on the medical device, step 1006, while the number of drops deposited is tracked and an estimated volume deposited is accumulated as per step 1008. The estimated volume deposited will be the number of drops deposited multiplied by the predicted single drop volume.

The "in-flight" volume of a drop or drops is captured, step 1010, where either every drop is measured or drops are measured at some sampling rate. A measured volume of deposited material, as a function of the captured "in-flight" volume measurement is then calculated, per step 1012. The measured volume is the number of drops deposited multiplied by the measured in-flight drop volume. The measured volume is then compared to the estimated value, step 1014, to determine if the coating process is operating according to plan.

At step 1016, the process is adjusted for any differences between the measured volume and the estimated volume. These adjustments include one or more of adjusting or changing the drop size, reducing the total number of drops to be deposited or increasing the number of drops to be deposited relative to the number of drops of material that were precalculated in step 1004.

In each of the on-line system 700 and the off-line system 700' an image of a drop is captured to determine a drop volume value. In one embodiment of the invention, an image of only one drop is captured during an exposure time as has been described above. In an alternate embodiment, multiple drops' images are captured during a single exposure time.

Figure 13:
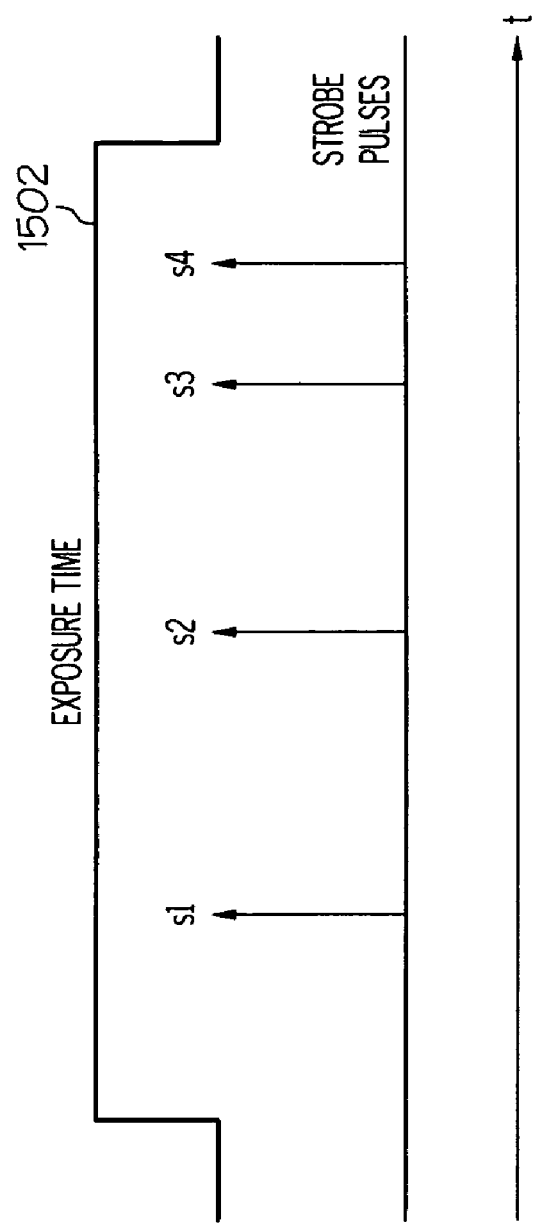
FIG. 13 is a timing chart for capturing multiple images of multiple drops during a single exposure period.

The imaging system 402 has an exposure time 1502, see FIG. 13, that spans across multiple sequential strobe light firings s1, s2, s3, s4 and, therefore, multiple sequential drops. As a result, the imaging system 402 captures the light from multiple drops that are fired during the exposure time 1502. This is analogous to multiple exposures in a single frame of a film camera.

Figure 14A:
FIGS. 14A-14G are representations of captured images.
Figure 14B:
Figure 14C:
Figure 14D:
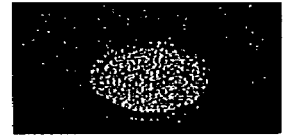
Figure 14E:
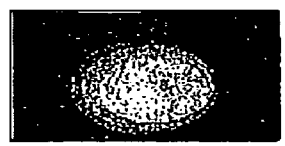
Figure 14F:

As a non-limiting example represented in FIGS. 14A-14G, therefore, four drops are fired during the exposure time 1502. After each strobe pulse, the image is changed. Thus, prior to the start of the exposure time, the image is represented in FIG. 14A. As the strobe fires s1, s2, s3, s4, the image will change as shown in FIGS. 14B, 14C, 14D, and 14E, respectively. These intermediate images are not "seen" or operated upon by this embodiment. The sensor is sampled after the end of the exposure time 1502. The image after strobe s4 is grabbed by the imaging system and transferred as a digital image. The present inventors have noted that the optics of the system slightly blurs the image and the processed image is shown in FIG. 14F.

The average drop image is determined from the image of FIG. 14F by applying edge detection techniques. One approach is to indicate local maximum slope as edge points. Advantageously, as a result of the multiple exposures, the addition to, or multiplication of, binary image pixels, i.e., the gray level values in the image, does not change the position of edge points. This represents an adaptive behavior of the drop shape detection.

Figure 14G:
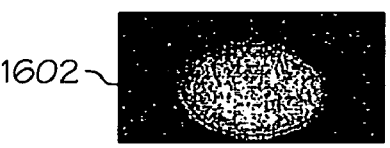

Alternatively, a local threshold value that changes from pixel to pixel in the image according to the dynamic range of the pixel's local neighborhood can be used to detect the edges of the image. Further, the local maximum slope technique and the local threshold value technique can be combined. The end result is a drop outline 1602 as shown in FIG. 14G. Once the outline is detected then the aforementioned techniques for determining volume can be applied.

The control system 302, in one embodiment of the present invention, is a general purpose personal computer or computing device implementing one or more applications programs to control and interact with the imaging system 402 and the user interface 408. The computer may run an operating system, as is known, such as Microsoft Windows, UNIX, Linux or Apple OS. The applications programs may be a combination of commercially available programs or programs written in any one of a number of available programming languages including, but not limited to, C, C++, JAVA, Pen and FORTRAN.

Figure 12:
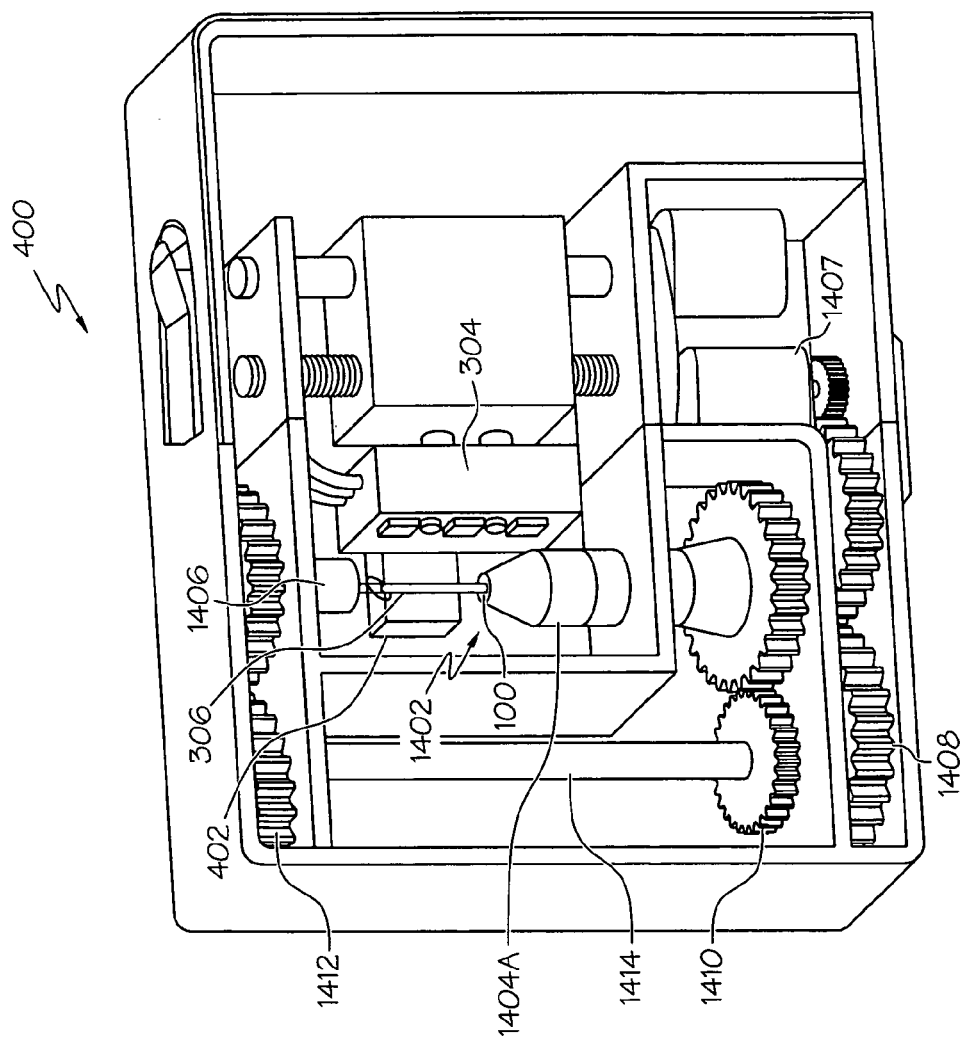
FIG. 12 is a schematic representation of a coating application system in accordance with one embodiment of the present invention.

One embodiment of the coating apparatus 400, as shown in FIG. 12, includes the imaging system 402 placed in position to image the coating drops as the drops are being applied. The stent 100 is deployed on the mandrel 306. The mandrel 306 with the stent 100 placed thereon is placed in an application compartment 1402 and held in position by a rotatable base 1404 and a rotatable upper holding element 1406, which are configured for substantially continued rotation, that is, they may complete a plurality of full 360 degree rotations, as required, during the coating process. The actual rotation may be substantially fully continuous (non-stop) or intermittent. The enclosed application compartment provides a sterile environment in which the coating process is performed. The rotation is actuated and synchronized by a stepper motor 1407 or the like and a gear system that includes gear clusters 1408, 1410, 1412 and shaft 1414. The motor is coupled to the control system 302. Alternatively, the gears may be replaced by drive belts, drive chains or any other mechanism that will maintain a synchronized drive, for example, two DC servo motors driven in a master/slave mode by the system controller. Of course, the system may be modified to accommodate a balloon mounted stent that is to be coated. Further, the DOD applicator can be configured to rotate in order to operate in the "off-line" embodiment described above with the appropriate placement of the imaging system.

One embodiment of the coating applicator 1104, as shown in FIG. 12, includes the imaging system 402 placed in position to image the coating drops as the drops are being applied. The stent 100 is deployed on the mandrel 306. The mandrel 306 with the stent 100 placed thereon is placed in an application compartment 1402 and held in position by a rotatable base 1404 and a rotatable upper holding element 1406, which are configured for substantially continued rotation, that is, they may complete a plurality of full 360 degree rotations, as required, during the coating process. The actual rotation may be substantially fully continuous (non-stop) or intermittent. The enclosed application compartment provides a sterile environment in which the coating process is performed. The rotation is actuated and synchronized by a stepper motor 1407 or the like and a gear system that includes gear clusters 1408, 1410, 1412 and shaft 1414. The motor is coupled to the control system 302. Alternatively, the gears may be replaced by drive belts, drive chains or any other mechanism that will maintain a synchronized drive, for example, two DC servo motors driven in a master/slave mode by the system controller. Of course, the system may be modified to accommodate a balloon mounted stent that is to be coated. Further, the DOD applicator can be configured to rotate in order to operate in the "off-line" embodiment described above with the appropriate placement of the imaging system.

Embodiments of the above-described invention may be implemented in either all software, all hardware, or a combination of hardware and software, including program code stored in a firmware format to support dedicated hardware. A software implementation of the above described embodiment(s) may comprise a series of computer instructions either fixed on a tangible medium, such as a computer readable media, e.g. diskette, CD-ROM, ROM, or fixed disk or transmittable to a computer system in a carrier wave, via a modem or other interface device. The medium can be either a tangible medium, including but not limited to optical or analog communications lines, or may be implemented with wireless techniques, including but not limited to microwave, infrared or other transmission techniques. The series of computer instructions whether contained in a tangible medium or a carrier wave embodies all or part of the functionality previously described herein with respect to the invention. Those skilled in the art will appreciate that such computer instructions can be written in a number of programming languages for use with many computer architectures or operating systems and may exist in machine executable format. Further, such instructions may be stored using any memory technology, present or future, including, but not limited to, semiconductor, magnetic, optical or other memory devices, or transmitted using any communications technology, present or future, including but not limited to optical, infrared, microwave, or other transmission technologies. It is contemplated that such a computer program product may be distributed as a removable media with accompanying printed or electronic documentation, e.g., shrink wrapped software, preloaded with a computer system, e.g., on system ROM or fixed disk, or distributed from a server or electronic bulletin board over a network, e.g., the Internet or World Wide Web.

Although various exemplary embodiments of the present invention have been disclosed, it will be apparent to those skilled in the art that changes and modifications can be made which will achieve some of the advantages of the invention without departing from the spirit and scope of the invention. It will be apparent to those reasonably skilled in the art that other components performing the same functions may be suitably substituted. Further, the methods of the invention may be achieved in either all software implementations, using the appropriate processor instructions, or in hybrid implementations that utilize a combination of hardware logic and software logic to achieve the same results.

What is claimed is:

1. A method of applying a coating to a surface of an implantable medical device, the method comprising:
depositing a plurality of drops of a coating material, each drop being deposited onto a predetermined location on the surface of the implantable medical device, each drop having a volume that is predetermined;
determining an in-flight volume of at least one of the plurality of drops comprising:
obtaining an image of a single drop after the drop has been ejected from an applicator and before the drop is deposited onto the predetermined location;
determining a drop volume measurement from the image comprising:
dividing the image of the drop into a number of slices from a first end of the image of the drop to a second end of the image of the drop;
determining the volume of each slice of the number of slices; and
adding the volumes of each of the number of slices to obtain the in-flight volume of the drop;
calculating a measured volume of the coating material that has been deposited onto the surface of the implantable medical device;
calculating a predicted volume of the coated material that has been deposited, the predicted volume being equal to the number of drops that have been deposited multiplied by the predetermined volume of each drop;
comparing the measured volume to the predicted volume; and
making an adjustment if the measured volume is different than the predicted volume, the adjustment consisting of modifying the predetermined volume of each drop, modifying a number of drops to be deposited, and any combination thereof, wherein a blocker is positioned so that at least one drop is deposited onto the blocker while making the adjustment.

2. The method of claim 1, further comprising:
performing a calibration procedure comprising:
placing an object with a known size in a field of view of an imaging system;
capturing an image of the object, the image having a diameter and comprising a plurality of pixels, each pixel having a first length and a second length;
determining a number of pixels across the diameter of the image;
calculating a unit of measurement per pixel, the unit of measure per pixel being equal to the diameter of the image divided by the number of pixels.

3. The method of claim 1, wherein capturing an image comprises:
capturing images of a plurality of drops during an exposure time.

4. A method of applying a coating to a surface of an implantable medical device, the method comprising:
depositing a plurality of drops of a coating material, each drop being deposited onto a predetermined location on the surface of the implantable medical device, each drop having a volume that is predetermined;
determining an in-flight volume of at least one of the plurality of drops comprising:
obtaining an image of a single drop after the drop has been ejected from an applicator and before the drop is deposited onto the predetermined location;
determining a drop volume measurement from the image comprising:
dividing the image of the drop into a number of slices from a first end of the image of the drop to a second end of the image of the drop;
determining the volume of each slice of the number of slices; and
adding the volumes of each of the number of slices to obtain the in-flight volume of the drop;
performing a calibration procedure comprising:
depositing at least one drop with a predetermined volume onto a target;
determining an in-flight volume of each of the at least one drop comprising:
obtaining an image of a single drop after the drop has been ejected from an applicator and before the drop is deposited onto the target;
determining a drop volume measurement from the image comprising:
dividing the image of the drop into a number of slices;
determining the volume of each slice of the number of slices; and
adding the volumes of each of the number of slices to obtain the in-flight volume of the drop;
determining a total drop volume, the total in-flight volume being equal to the sum of each drop volume measurement determined; and
determining an actual volume of the at least one drop deposited onto the target; comparing the actual volume to the total drop volume.

5. The method of claim 4, the plurality of drops being deposited by an applicator, the applicator facing a first direction during the calibration procedure and a second direction during the depositing of the plurality of drops, the applicator facing away from the implantable medical device in first direction and facing towards the implantable medical device in the second direction.

6. A method of depositing material onto a surface of a medical device, the method comprising:
depositing a plurality of drops of material onto the surface of the medical device, each drop being deposited onto a predetermined location, each drop having a predetermined volume;
determining an average drop volume comprising:
capturing an image, the image comprising a plurality of sequential drops of the plurality of drops after each drop has been emitted from an applicator, the image being captured with an imaging system, the imaging system having an exposure time, a plurality of sequential strobe light firings occurring during the exposure time, each strobe light firing illuminating a different drop of the plurality of sequential drops;
determining an outline of an average drop image of the plurality of sequential drops captured in the image by applying an edge detection technique;
determining an average drop volume from the outline of the average drop image.

7. The method of claim 6, further comprising:
calculating a measured volume of material that has been deposited after a first number of drops have been deposited onto the surface of the medical device the measured volume being equal to the first number of drops multiplied by the average drop volume;

calculating a predicted volume of the material that has been deposited, the predicted volume being equal to the first number of drops multiplied by the predetermined volume of each drop;

comparing the measured volume to the predicted volume and making an adjustment if the measured volume is different than the predicted volume, the adjustment consisting of modifying the predetermined volume of each drop, modifying a number of drops to be deposited, and any combination thereof.

* * * * *